(12) United States Patent
Berk et al.

(10) Patent No.: US 7,433,806 B2
(45) Date of Patent: Oct. 7, 2008

(54) BAND MODEL METHOD FOR MODELING ATMOSPHERIC PROPAGATION AT ARBITRARILY FINE SPECTRAL RESOLUTION

(75) Inventors: Alexander Berk, Sharon, MA (US); Prabhat K. Acharya, Burlington, MA (US); Lawrence S. Bernstein, Lexington, MA (US); Gail P. Anderson, Boulder, CO (US); Paul Lewis, Falls Church, VA (US); James H. Chetwynd, Stoneham, MA (US); Michael L. Hoke, Leominster, MA (US)

(73) Assignee: Spectral Sciences, Inc., Burlington, MA (US)

( * ) Notice: Subject to any disclaimer, the term of this patent is extended or adjusted under 35 U.S.C. 154(b) by 445 days.

(21) Appl. No.: 09/838,801

(22) Filed: Apr. 20, 2001

(65) Prior Publication Data

US 2003/0096425 A1    May 22, 2003

(51) Int. Cl.
  *G06G 7/48*     (2006.01)
  *G06K 9/40*     (2006.01)
  *G01N 30/90*    (2006.01)
  *G01N 21/62*    (2006.01)
  *G01N 1/22*     (2006.01)

(52) U.S. Cl. .................. 703/2; 382/274; 73/23.37; 436/171; 436/181

(58) Field of Classification Search .............. 703/2, 703/24, 28, 30; 702/24, 28, 30, 2; 436/171, 436/181; 73/61, 23.37; 382/274
See application file for complete search history.

(56) References Cited

U.S. PATENT DOCUMENTS 5,315,513 A * 5/1994 Abreu et al. ............... 702/3

OTHER PUBLICATIONS

Piters et al, "A Combined Fourier-Bessel Transformation Method to Derive Accurate Rotational Velocities", Astronomy and Astrophysics Supplement Series 118, 1996, pp. 529-544.*
Martin et al, "Generalized Lorentzian Approximations for the Voigt Line Shape" Applied Optics, vol. 20, No. 2, Jan. 1981, pp. 259-263.*
Weisstein, Eric, CRC Concise Encyclopedia of Mathematics, Chapman & Hall/CRC, 1999, pp. 1297-1298.*
Gossage et al., "MOD3D: A Model for Incorporating MODTRAN radiative Transfer inot 3D Simulations", Apr. 2001. Spectal Sciences (White Paper) p. 1-8.*
Acharya et al., "MODTRAN4: Multiple Scattering and BI-Directional Reflectance Distribution Function (BRDF) Upgrades to MODTRAN". Jul. 1999. Spetral Sciences (White Papter) p. 1-11.*

(Continued)

*Primary Examiner*—Albert DeCady
*Assistant Examiner*—Thomas H Stevens
(74) *Attorney, Agent, or Firm*—Brian M. Dingman; Mirick, O'Connell, DeMallie & Lougee

(57) ABSTRACT

A radiative transport band model algorithm has been developed for prediction and analysis of high spectral resolution radiometric measurements. Atomic and molecular line center absorption is determined from finite spectral bin equivalent widths. A new mathematically exact expansion for finite bin equivalent widths provides high accuracy at any desired spectral resolution. The temperature and pressure dependent Voigt line tail spectral absorption contributing to each spectral bin is pre-computed and fit to Padé approximants for rapid and accurate accounting of neighboring-to-distant lines.

28 Claims, 12 Drawing Sheets

OTHER PUBLICATIONS

MODTRAN: A Moderate Resolution Model for LOWTRAN; Berk et al., Spectral Sciences Inc., Burlington, MA Technical Report May 12, 1986-May 11, 1987, abstract, p. 1-2.*

Halthore et al., "Models Overestimate Diffuse Clear-Sky Surface Irradiance: A Case for Excess Atmospheric Absorption" 1998 Spectral Science p. 3591-3594.*

Berk et al., "Reformulation of the MODTRAN Band Model for Higher Spectral Resolution". Apr. 2000, p. 1-10.*

MODTRAN 4 User's Manual, Air Force Research Lab Hanscom AFB 1999 p. 1-95.*

MODTRAN Cloud and Multiple Scattering Upgrades with Application to AVIRS 1998 p. 368-375.*

Wan et al., "Effects to Temperature-Dependent Molecular Absorption of the Thermal Infrared Remote Sensing of the Earth Surface", IGARSS 1992 p. 1242-1245.*

* cited by examiner (PRIOR ART)

BAND MODEL METHOD FOR MODELING ATMOSPHERIC PROPAGATION AT ARBITRARILY FINE SPECTRAL RESOLUTION

GOVERNMENT RIGHTS

This invention was made with Government support under Contract No. F19628-98-C-0050 awarded by the Department of the Air Force. The Government has certain rights in this invention.

FIELD OF THE INVENTION

This invention relates to a radiative transport band model for application to high spectral resolution simulations.

BACKGROUND OF THE INVENTION

MODTRAN4 is the U.S. Air Force (USAF) standard moderate (2 $cm^{-1}$) or broader/coarser spectral resolution radiative transport (RT) model for wavelengths extending from the thermal InfraRed (IR) through the visible and into the ultraviolet (0.2 to 10,000.0 μm). [See: A. Berk, G. P. Anderson, P. K. Acharya, L. S. Bernstein, J. H. Chetwynd, M. W. Matthew, E. P. Shettle and S. M. Adler-Golden, "MODTRAN4 User's Manual," Air Force Research Laboratory Report, June 1999, and see: A. Berk, L. S. Bernstein, G. P. Anderson, P. K. Acharya, D. C. Robertson, J. H. Chetwynd and S. M. Adler-Golden, "MODTRAN Cloud and Multiple Scattering Upgrades with Application to AVIRIS," Remote Sens. Environ. 65, pp. 367-375, 1998.]

The MODTRAN4 1 $cm^{-1}$ statistical band model (from which 2 $cm^{-1}$ spectral resolution results are obtained) provides a fast alternative (100-fold increase in speed) to the USAF more accurate line-by-line (LBL) radiative transport models, FASCODE and FASE. [See: S. A. Clough, F. X. Kneizys, G. P. Anderson, E. P. Shettle, J. H. Chetwynd, L. W. Abreu, and L. A. Hall, "FASCODE3 Spectral Simulation," *Proceedings of the International Radiation Symposium*, Lenoble and Geleyn, Deepak Publishing, 1988, and see: H. E. Snell, J. -L. Moncet, G. P. Anderson, J. H. Chetwynd, S. Miller, and J. Wang, "FASCODE for the Environment (FASE)", *Proceedings of Atmospheric Propagation and Remote Sensing IV, SPIE*, 2471, pp. 88-95, 1995.] FASCODE and FASE are both based on a 'first principles' physical equations, expanding the optical depth terms, based on spectroscopic constants and line shape, with very high accuracy. Comparisons between MODTRAN4 and FASE spectral transmittances and radiances show agreement to within a few percent or better in the thermal IR. MODTRAN4 includes flux and atmosphere-scattered solar calculations, essential components in analysis of near-IR, visible and ultraviolet spectral region data that are not readily generated by LBL models.

MODTRAN4 and its predecessors have been used extensively over the last quarter century in the design and analysis of broadband, multiband, and short-wave IR/Visible hyperspectral imaging sensors. However, conventional interferometers and many state-of-the-art sensors working in the long- and mid-wave IR operate at higher spectral resolution than MODTRAN4 provides.

Narrowing the band model spectral resolution changes the fundamental character of the band model. The half-width of molecular transitions near sea level average about 0.08 $cm^{-1}$. As illustrated in FIG. 1(a), the 1.0 $cm^{-1}$ band model calculates the absorption of atomic and molecular lines whose line center regions lie almost entirely within the spectral bin. At the finer spectral resolution, a much larger fraction of any atomic or molecular line falls outside of the spectral bin containing the line. Determination of the new band model has therefore required improved treatment of both line tail and line center absorption. Line tail absorption is modeled closer to line centers (as defined by a compilation of spectroscopic data), and the finite-bin single-line equivalent width used to calculate line center absorption is no longer simply a small perturbation of the total single line equivalent width.

The line center absorption within a spectral bin is generally defined as the in-band absorption from all atomic and molecular transitions centered in that bin, FIG. 2. LBL models calculate this in-band absorption by explicitly determining the spectral absorption of each line on a very fine spectral grid and then integrating the resulting spectrum. In a band model approach, the in-band absorption is approximated based on statistical assumptions regarding line positions and overlap. Temperature dependent band model parameters are computed from an atomic and molecular transition line atlas such as HITRAN. [See L. S. Rothman, C. P. Rinsland, A. Goldman, S. T. Massie, D. P. Edwards, J. -M. Flaud, A. Perrin, V. Dana, J.-. Y. Mandin, J. Schroeder, A. McCann, R. R. Gamache, R. B. Wattson, K. Yoshino, K. Chance, K. W. Jucks, L. R. Brown, V. Nemtchinov, and P. Varanasi, The HITRAN Atomic and molecular Spectroscopic Database and HAWKS (HITRAN Atmospheric Workstation): 1996 Edition, *J. Quant. Spectrosc. Radiat. Transfer*, 60, pp. 665-710 (1998)]. These parameters define an effective single-line for the interval, characterized by its absorption line strength and half-width parameters, and the effective number of lines, $n_{eff}$.

In MODTRAN4, the finite spectral bin single-line Voigt equivalent width $W_{sl}$ is computed to determine the absorption of the effective average line. It is calculated as the difference between the total equivalent width, computed using the Rodgers-Williams formula [see: C. D. Rodgers and A. P. Williams, "Integrated absorption of a spectral line with the Voigt profile", *J. Quant. Spectrosc. Radiat. Transfer*, 14, pp. 319-323, 1974], and the absorption due to the two line tails falling outside of the spectral band. The line tail calculations are performed for a line centered 0.2 $cm^{-1}$ from the edge of the 1.0 $cm^{-1}$ spectral bin; offsetting the location of the effective line from the center of the bin gives a more representative result for the average absorption of the two line tails. MODTRAN4 computes the line tail absorption by modeling the tail line-shape as being inversely proportional to the square of the line center displacement, i.e., $\propto (\Delta v)^{-2}$. With lines centered 0.2 $cm^{-1}$ from the edge of the spectral band, Doppler contributions to the line tails are small and the Lorentz line-shape denominator is dominated by the line center displacement term for Lorentz half-widths less than about 0.1 $cm^{-1}$.

MODTRAN4 1.0 $cm^{-1}$ band model line tail absorption is defined as the absorption from molecular transitions centered outside of the 1.0 $cm^{-1}$ band but no more than 25 $cm^{-1}$ from band center. Contributions from beyond 25 $cm^{-1}$ are only considered for $H_2O$ and $CO_2$, and modeled as continua (based on the approach in FASCODE). The line tail absorption is calculated from a database of temperature dependent 0.25 $cm^{-1}$ integrated Lorentzian absorption coefficients. The line tail spectral dependence is assumed to be relatively flat so that the absorption coefficients can be modeled as constant over the 0.25 $cm^{-1}$ spectral grid. To justify this assumption and enable line tails to be modeled as Lorentzian, atomic and molecular transitions centered too close to a 1.0 $cm^{-1}$ spectral band edge are translated inward. A small line-shift correction is applied in-band to preserve the total integrated line strength. The overall error introduced into the 1.0 cm$^{-1}$ band model by shifting line centers is small.

MODTRAN4 computes the total 1.0 cm$^{-1}$ spectral band transmittance $T_v$ for the $n_{eff}$ identical lines by assuming line overlap characteristic of randomly distributed lines within a spectral interval. Plass [see: G. N. Plass, "Models for Spectral Band Absorption", *J. Opt. Soc. Am.*, 48, pp. 690-703, 1958] showed that the transmittance due to randomly distributed identical lines is given by the expression $$T_v = \left(1 - \frac{W_{sl}}{\Delta v}\right)^{n_{eff}}. \tag{1}$$

The Plass transmittance reduces to exact expressions in the limit of a single line, $T_v(n_{eff}=1)=1-W_{sl}/\Delta v$, and in the many line limit, $T_v(n_{eff}\to\infty)=\exp(-n_{eff}W_{sl}/\Delta v)$.

As spectral resolution narrows, direct application of the MODTRAN4 band model becomes inaccurate. With a $\Delta v=0.1$ cm$^{-1}$ spectral bandwidth, for example, and an effective average line positioned 0.25 $\Delta v$ from the bin edge, line tail absorption at 1 atm pressure contains significant Voigt contributions, and the MODTRAN algorithm is not applicable in this regime.

SUMMARY OF THE INVENTION

SERTRAN, a Spectrally Enhanced Resolution extension of MODTRAN, has been developed and its radiative transfer algorithm is described and claimed herein. SERTRAN retains all MODTRAN4 capabilities while providing a factor of up to ten improvement in spectral resolution. Due to its finer spectral resolution, SERTRAN improves treatment of line correlation and increases overall accuracy when compared to MODTRAN4. Because of the increased computational complexity, SERTRAN runs somewhat slower than the MODTRAN4 1 cm$^{-1}$ binned band model, but is still considerably faster than LBL radiative transport models.

The MODTRAN4 and SERTRAN band models do share major radiative transport elements. The basic quantities computed by the band models are individual species spectral transmittances through homogeneous path segments. These segments are defined within single atmospheric layers if the Correlated-k (CK) [see: L. S. Bernstein, A. Berk, D. C. Robertson, P. K. Acharya, G. P. Anderson, and J. H. Chetwynd, "Addition of a Correlated-k Capability to MODTRAN," *Proceedings of the 1996 Meeting of the IRIS Specialty Group on Targets, Backgrounds, and Discrimination*, Vol. III, pp. 249-258, 1996] algorithm is selected and for Curtis-Godson averaged paths [see: A. R. Curtis, Contribution to a Discussion of "A Statistical Model for Water Vapor Absorption," by R. M. Goody, *Quart. J Roy. Meteorol. Soc*. 78, pp. 638-640, 1952, and see: W. L. Godson, "The Evaluation of Infrared-Radiative Fluxes Due to Atmospheric Water Vapor," *Quart. J. Roy. Meteorol. Soc*. 79, pp. 367-379, 1953] otherwise. The individual species transmittances are themselves computed as a product of three terms: the molecular continuum ($\Delta v>25$ cm$^{-1}$), line tails and line centers. Only the line tail and line center calculations differ between the MODTRAN4 and SERTRAN band models.

This invention features a band model method for computing individual atomic and molecular species spectral transmittances through a gaseous medium, comprising: dividing the spectral region being considered into a number of spectral bins, each having a width of less than 1.0 cm$^{-1}$; calculating the equivalent width of atomic and molecular transitions centered within each spectral bin; and calculating line tail absorption within each spectral bin from atomic and molecular transitions not centered within the bin.

The spectral bins may have a width of about 0.1 cm$^{-1}$. The calculating step may include an exact expansion for calculating the bin Voigt equivalent width of atomic and molecular transitions whose centers lie within each spectral bin. The exact expansion is preferably an exact modified Bessel functions expansion. The calculating step may include subtracting the line-tail absorption as calculated from the column strength, the Lorentz half-width, the Doppler half-width, and the line tail spectral displacement. The calculating step may include determining the Voigt line-shape function at specific spectral frequencies.

The line tail calculation step may include calculating line tail absorption within each bin from atomic and molecular transitions centered outside of the bin using Padé approximant spectral fits to Voigt absorption coefficient curves. The line tail absorption calculation step may include determining a database of temperature and pressure dependent Padé approximant spectral fits to Voigt absorption coefficient curves. There may be five Padé parameters. The Padé parameters may be determined from summed line tail spectral absorption coefficients. One Padé parameter may be determined at the center of the bin, and one at each edge of the bin, and one may be the derivative of the absorption coefficient with respect to the normalized spectral variable at the line center, and one may be the integral of the spectral absorption coefficient over the spectral band. The Padé parameter database is preferably generated for a plurality of temperatures and pressures.

Another embodiment of the invention features a band model method for determining the contribution of line centers to the computation of individual atomic and molecular species spectral transmittances through a gaseous medium, comprising: dividing the spectrum being measured into a number of spectral bins; and calculating the bin Voigt equivalent width of atomic and molecular transitions centered within each spectral bin from an exact expansion.

Yet another embodiment features a method for determining the contribution of line tails to the computation of individual atomic and molecular species spectral transmittances through a gaseous medium, comprising: dividing the spectral region being considered into a number of spectral bins; and calculating line tail absorption within each bin from atomic and molecular transitions centered outside of the bin using Padé approximant spectral fits to Voigt absorption coefficient curves.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

Figure 1:
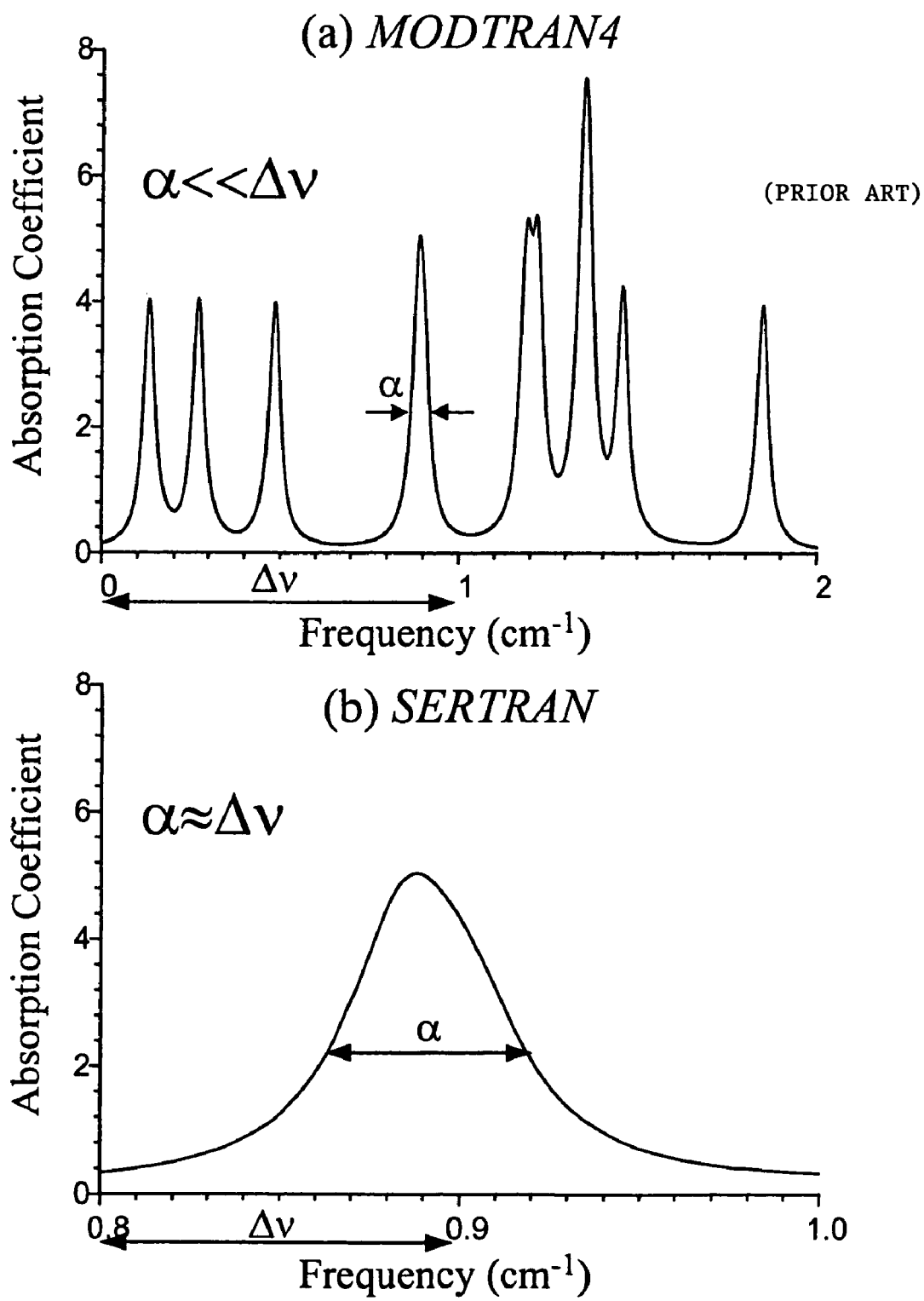
FIG. 1 displays molecular transition spectral absorption near the ground: (a) Spectral features within a 1.0 cm$^{-1}$ bin; (b) Spectral features within a 0.1 cm$^{-1}$ bin.
Figure 2:
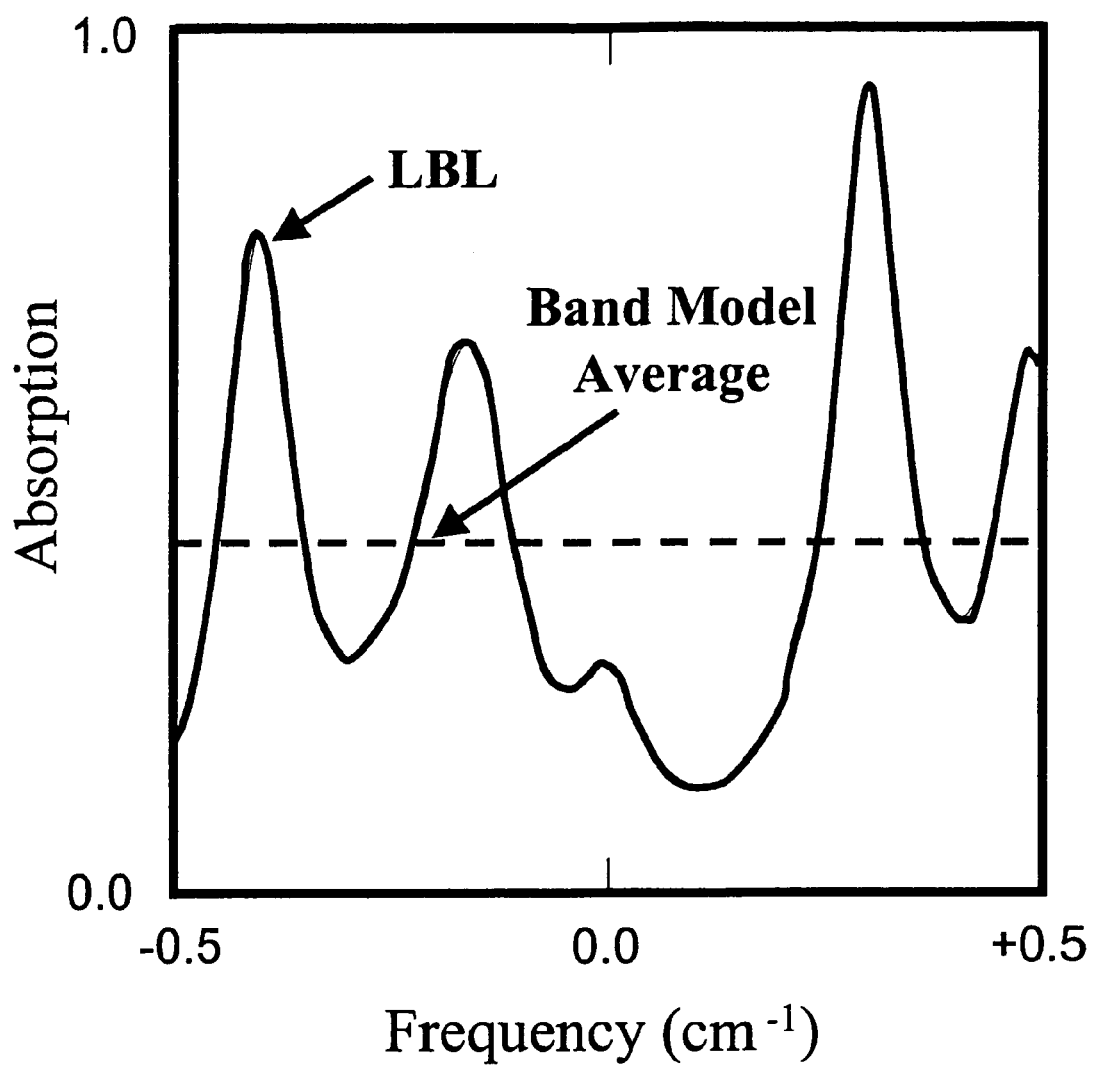
FIG. 2 is a comparison of Band Model and Line-By-Line Approaches. LBL models calculate high spectral resolution absorption (solid curve). Band models statistically determine the average integrated strength (dash line) based on line strength, line density, and line width parameters.

Two RT algorithms have been implemented in SERTRAN. The two options are referred to as the "single-bin" and "double-bin" approaches. The "single-bin" approach is preferred for highest spectral resolution calculations, and it uses the traditional partitioning of the atomic and molecular line absorption contributions to a spectral bin. Line center absorption is defined as the absorption from all lines centered within the bin, and the line tail absorption is defined as the contribution from all lines centered outside of the bin, but within a pre-selected cutoff distance (25 $cm^{-1}$ in MODTRAN and SERTRAN). As is common in band model theory, an effective average line is defined for calculation of the line center absorption. The finite bin equivalent width of that line is computed with the line centered one-quarter of a bin-width from one bin edge and three-quarters of a bin-width from the other edge. New algorithms described below are required to accurately and efficiently compute the finite-bin equivalent width for bin-widths of size comparable to the line width. The temperature and pressure dependent spectral absorption from line tails is pre-computed and fit to Padé approximants. In the line tail computations, lines centered too close to a spectral bin edge, i.e., within a quarter of a bin-width, are translated to the quarter bin-width position in order to avoid modeling their line centers as a line tails.

The alternative "double-bin" band model approach was introduced into SERTRAN to simplify the line center calculations and improve upon the line tail algorithm. The SERTRAN "double-bin" approach defines the band model line center absorption as the in-bin absorption from all lines centered in the selected bin and all lines centered within half a bin-width of the selected bin. With this definition, the line center absorption of each atomic and molecular transition is partitioned between two spectral bins, the one in which the line is located and its nearest neighbor—hence, the name "double-bin". On average, half the lines contributing to the interval are centered in the interval and half are centered outside the interval. Thus, the finite-bin equivalent width is computed for a line centered precisely on the edge of the spectral bin. For 0.1 $cm^{-1}$ spectral bins, the total in-band absorption from the edge-centered line equals one-half the difference between the total equivalent width of the line and the 0.1 $cm^{-1}$ tail. This simplifies the line center calculation because only a single line tail must be computed, and, more importantly, the line tail begins a full bin-width from line center instead of at the quarter of a bin-width point. The other advantage of the "double-bin" over the "single-bin" approach is that the line tail absorption by definition only includes the contribution from lines centered more than half a bin-width from a given bin. Thus, the position of line centers does not have to be translated to avoid modeling line centers as line tails.

The disadvantage of the "double-bin" approach is that the line center absorption from lines which are narrow compared to the bin-width is evenly partitioned between two bins when in reality the absorption essentially occurs in a single bin unless the line happens to be positioned at the bin edge. The consequence of this incorrect partitioning is that the resolution of the band model is reduced. Thus, a 0.1 $cm^{-1}$ "double-bin" band model actually provides spectral resolution comparable to a 0.2 $cm^{-1}$ "single-bin" band model. For this reason, highest spectral resolution calculations should be performed with the "single-bin" method. Of course, the bin-width in the double-bin method could be reduced to 0.05 $cm^{-1}$ to be comparable to the single-bin 0.1 $cm^{-1}$ implementation, but this would double the size of the required databases and eliminate much of the computation simplicity of the line center computation (because the line tail offset has been reduced by a half).

Since atmospheric molecular line half-widths can be as large as 0.13 $cm^{-1}$, the 0.1 $cm^{-1}$ line tails used in the double-bin approach as implemented in SERTRAN (or worse yet the 0.025 $cm^{-1}$ line tails required for the single-bin approach) cannot be modeled as simply being inversely proportional to the square of the line center displacement. A description of the upgraded algorithm for line tail absorption follows.

SERTRAN Band Model Line Tail Absorption

For SERTRAN, with its $\Delta v = 0.1$ $cm^{-1}$ band model, the MODTRAN4 line tail algorithm is inappropriate. Line tail spectral absorption cannot be modeled as constant or even Lorentzian so close to line center. SERTRAN greatly improves upon the MODTRAN approach by defining a database of temperature- and pressure-dependent Padé approximant spectral fits to Voigt absorption coefficient curves, $k(\delta_v)$. Five parameters, $k_0$, $k_1$, $k_2$, $x_1$ and $x_2$, are used in the Padé fits:

$$\frac{k(\delta_v)}{P} = \frac{k_0 + k_1 \delta_v + k_2 \delta_v^2}{1 + x_1 \delta_v + x_2 \delta_v^2}; \delta_v = \frac{v - v_{cen}}{\Delta v/2}. \quad (2)$$

In this parameterization, $v_{cen}$ is the central frequency of the spectral band and the range of the normalized spectral variable $\delta_v$ is from −1 to +1. Since the Lorentz line shape is proportional to pressure to leading order, the absorption coefficient over pressure P is fit to the Padé approximant. This form for the tail contributions yields an exact spectral fit in the limit of a single Lorentz tail. The five Padé parameters are determined from the summed line tail spectral absorption coefficients at the center and edges of the spectral band, k(0), k(−1) and k(+1), the derivative of the absorption coefficient with respect to $\delta_v$ at $v_{cen}$, k'(0), and the integral of the spectral absorption coefficient over the spectral band, $\int_{[-1,+1]} k(\delta_v) d\delta_v$. The values of $x_1$ and $x_2$ are restricted to insure no singularities for $\delta_v$ in [−1, +1]. No exact solution exists for the Padé parameters in a very limited number of cases, approximately 1 in 100,000. Essentially, the spectral absorption coefficient data are too restrictive to allow the integral condition to be satisfied. In these cases, the derivative constraint is relaxed to enable the integrated absorption coefficient to be preserved.

Figure 3:
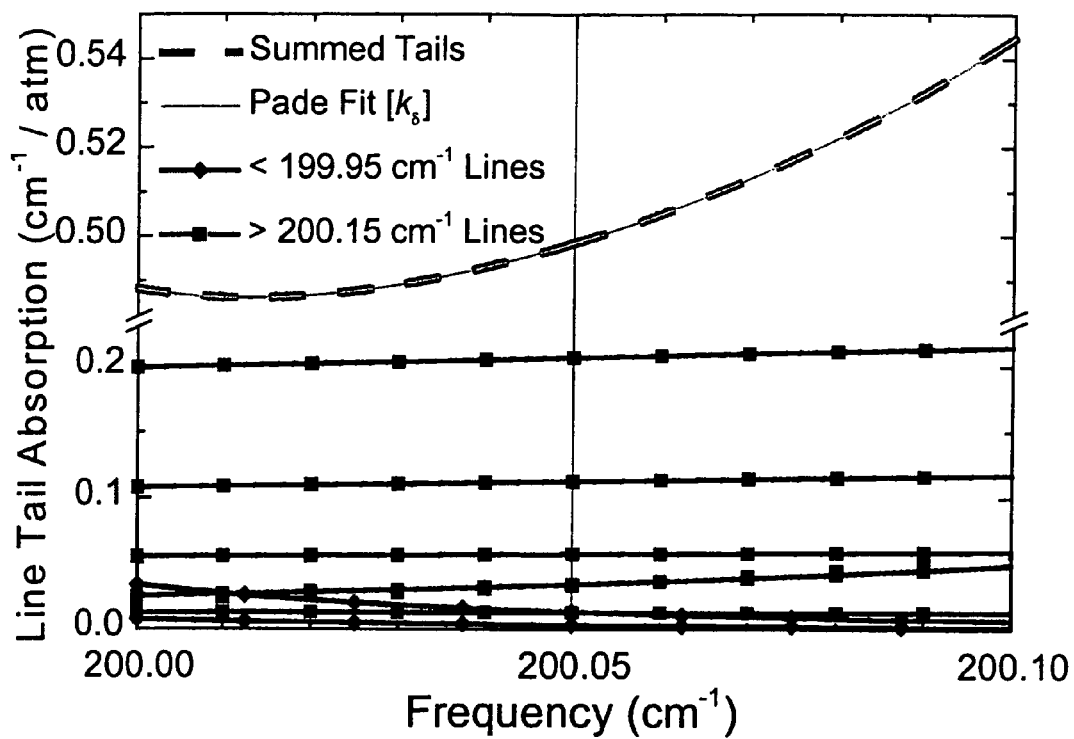
FIG. 3 shows a High Spectral Resolution Line Tail Absorption Curve (thick dash) and Padé Approximant Fit (thin line) for Lorentzian $H_2O$ Lines at 305K and 1 atm Pressure. The spectral curves from largest contributors are also illustrated (lines with diamond for lower frequency transitions and lines with squares for higher frequency transitions).

Generally, the Padé spectral fits are extremely accurate. An example is shown in FIG. 3. In this case, hundreds of molecular transitions contribute to the 305K and 1 atm pressure $H_2O$ line tail absorption coefficient spectrum between 200.0 and 200.1 cm$^{-1}$, the thick dashed curve. The six largest contributors to the curve from lines centered above 200.15 cm$^{-1}$ are shown as lines with squares, and the two largest contributors from lines centered below 199.95 cm$^{-1}$ are shown as lines with diamonds (note the break and change of scale in the ordinate axis). As described above, the Padé fit fixes the spectral curve values at 200.00, 200.05, and 200.10 cm$^{-1}$, the spectral derivative at 200.05 cm$^{-1}$, and the integrated value. In this case, as with most, the spectral fit lies directly on top of the high-resolution spectrum.

Figure 4:
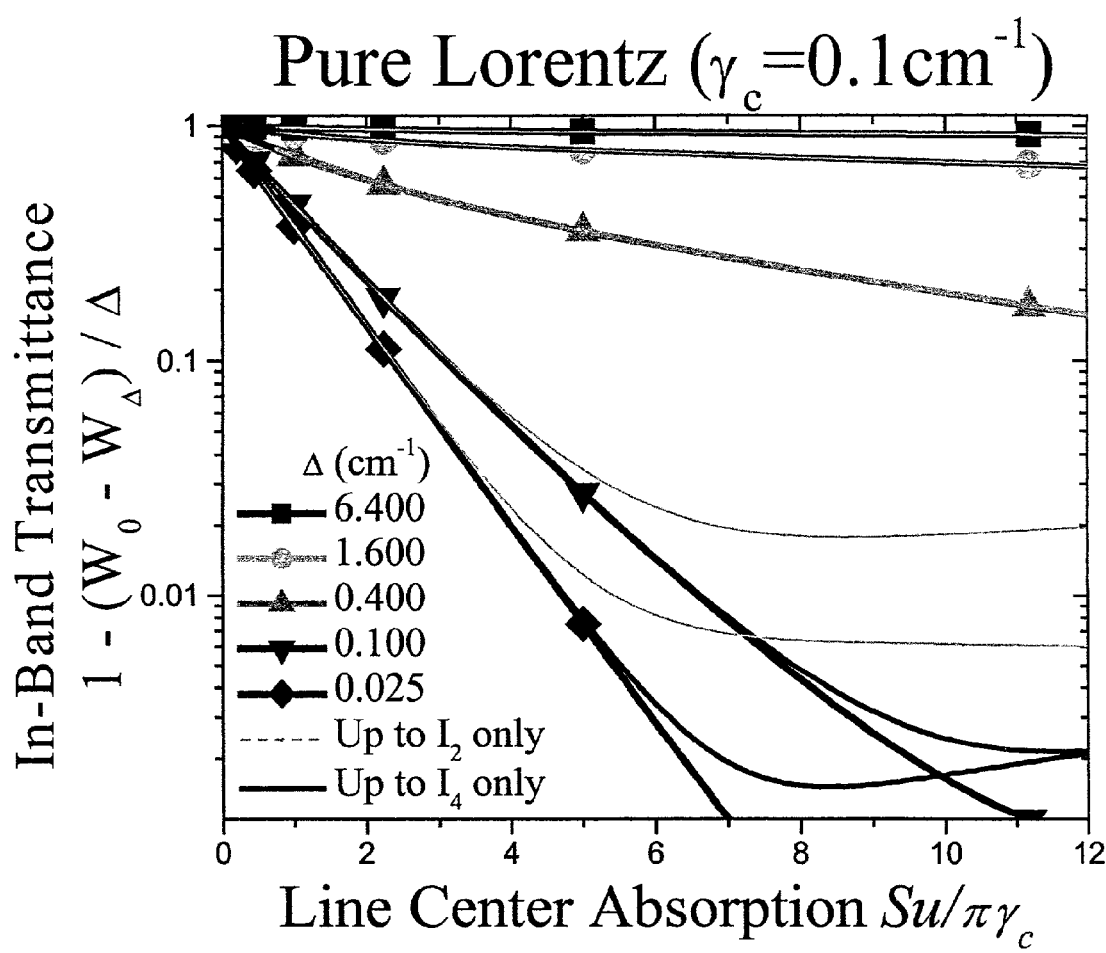
FIG. 4 is a High Spectral Resolution Line Tail Absorption Curve (dash) and Padé Approximant Fit (solid) for Voigt lines with Strong Doppler Influence. The lower curve is the residual between the upper curves.

The spectral fit to the line tails is least accurate but still quite acceptable when the Doppler contribution is strong. The Padé form is unable to completely mimic the exponential decay of the Doppler line shape. For SERTRAN molecular bands, the worse fits result from near-IR $O_2$ lines and near-IR and visible $H_2O$ lines. In the example of FIG. 4, the Doppler half-widths for the contributing $H_2O$ lines are near 0.019 cm$^{-1}$ and the atmospheric pressure is 0.1 atm. Although the Padé fit satisfies the 5 prescribed conditions, small but apparent residuals result.

In the preferred embodiment, the SERTRAN Padé parameter database is generated for six temperatures from 180 to 305K, and for pressures of 1.0 and 0.1 atm. In SERTRAN, the user can set the parameter which defines the number of monochromatic line tail absorption coefficient calculations performed per 0.1 cm$^{-1}$ spectral bin; it is nominally set to five. The line tail optical depth is modeled as varying linearly between spectral points. The monochromatic line tail optical depth and thermal emission calculations can be summed through multiple atmospheric layers, with the in-band (0.1 cm$^{-1}$) transmittance integrated as the final step.

In principle, one could perform multiple scattering calculations at the spectral resolution defined by the sub-division of the spectral bin; however this procedure would be computationally expensive and inconsistently mesh with the band model line center optical depths, which are already spectrally averaged. Thus, unless the correlated-k algorithm is selected, the multiple scattering calculations are performed with in-band optical depths defined for each layer.

If a correlated-k option is invoked for computing molecular absorption, then the spectral line tail optical depth must be distributed among the k-intervals. The procedure for partitioning the line tails is not well defined. The mapping from absorption coefficient value to frequency is not necessarily fully correlated for multiple path segments, and the mapping is generally lost in the construction of k-distributions. In fact, in the MODTRAN4 correlated-k algorithm, the k-distributions are statistical representations based on the band model parameters; no exact mapping back to frequency space even exists. However, since the band model is based on a random distribution of line centers, a random partitioning of the line tail absorption among the k-intervals is a consistent approach. In SERTRAN, the partitioning is fixed, not random, but it is defined to insure that the strongest line center absorption features are well distributed over the spectral-bin.

Generalizing the Ladenburg and Reiche Equivalent Width Formula for Treatment of Voigt Lines and Finite Spectral Bins Introduction Band model radiative transport models such as MODTRAN and SERTRAN [see A. Berk, L. S. Bernstein, G. P. Anderson, P. K. Acharya, D. C. Robertson, J. H. Chetwynd, and S. M. Adler-Golden, MODTRAN Cloud and Multiple Scattering Upgrades with Application to AVIRIS, *Remote Sens. Environ.*, 65, 367-375 (1998), and see A. Berk, P. K. Acharya, L. S. Bernstein, G. P. Anderson, J. H. Chetwynd, and M. L. Hoke, "Reformulation of the MODTRAN band model for higher spectral resolution," in *Algorithms for Multispectral, Hyperspectral, and Ultraspectral Imagery VI*, Sylvia S. Shen, Michael R Descour, Editors, Proceedings of SPIE Vol. 4049, 190-198 (2000)] provide accurate and efficient methods for computing in-band atmospheric transmittances, radiances and fluxes. These models pre-process molecular transition data like that in the HITRAN database [see L. S. Rothman, C. P. Rinsland, A. Goldman, S. T. Massie, D. P. Edwards, J. -M. Flaud, A. Perrin, V. Dana, J.-. Y. Mandin, J. Schroeder, A. McCann, R. R. Gamache, R. B. Wattson, K. Yoshino, K. Chance, K. W. Jucks, L. R. Brown, V. Nemtchinov, and P. Varanasi, The HITRAN Molecular Spectroscopic Database and HAWKS (HITRAN Atmospheric Workstation): 1996 Edition, *J. Quant. Spectrosc. Radiat. Transfer*, 60, pp. 665-710 (1998)] to define temperature-dependent total line strengths, temperature-dependent effective numbers of lines, an average collision (Lorentz) half-width at standard pressure, and line-tail absorption coefficients for each molecular absorption source in finite spectral bands. These parameters along with the Doppler half-width are used to define statistically averaged molecular absorption lines within homogeneous path segments. The path segments are specified by their temperature, pressure, molecular abundances and path length. The in-band absorption or equivalently the finite bin Voigt equivalent width of the statistically averaged molecular lines is computed and combined with line position and strength distribution assumptions [see: G. N. Plass, Models for Spectral Band Absorption, *J. Opt. Soc. Am.*, 48, 690-703, (1958), see: D. C. Robertson, L. S. Bernstein, R. Haimes, J. Wunderlich, and L. Vega, 5 cm$^{-1}$ Band Model Option to LOWTRAN 5, *Appl. Opt.*, 20, 3218-3226 (1981), and see: R. M. Goody and Y. L. Yung, *Atmospheric Radiation:*

*Theoretical Basis*, 2$^{nd}$ ed., (New York, Oxford University Press, 1989)] to determine the in-band transmittance.

The band model approach provides a major advantage over the more rigorous line-by-line (LBL) technique in that in-band values are computed directly. In LBL calculations, spectral optical depths are determined at a very high spectral resolution (typically, 0.01 to 0.0001 cm$^{-1}$) and then transmittances are spectrally integrated to obtain the in-band values. At each spectral point, the absorption from all contributing atomic and molecular lines must be computed and summed. In the long wave infrared, hundreds-to-thousands of lines often contribute significantly to a single spectral point. It is for this reason that a statistical approach is beneficial and often crucial for solving real world problems.

With the increasing signal-to-noise, spectral resolution and data flow of current and developmental infrared optical sensor, there is a desire and requirement to improve band models so that finer spectral resolution and higher accuracy predictions can be quickly generated. A critical aspect of this development is the calculation of accurate equivalent widths. The standard approach for calculating finite spectral bin equivalent widths involves computing the total line absorption i.e., total equivalent width, and then subtracting the two line-tail contributions. At moderate spectral resolution ($\geq 1.0$ cm$^{-1}$), the total equivalent width can be computed by interpolating between the pure Doppler and Lorentz total equivalent widths [see: C. D. Rodgers and A. P. Williams, Integrated absorption of a spectral line with the Voigt profile, *J Quant. Spectrosc. Radiat. Transfer*, 14, 319-323, (1974)], and the line-tail contributions determined from the reciprocal-frequency squared drop off of the line shape.

The development of a higher spectral resolution ($\cong 0.1$ cm$^{-1}$) band model requires highly accurate total and line-tail equivalent width calculations. When the frequency displacement from line center to line-tail is small compared to the Lorentz or Doppler half widths, the magnitude of the two terms being differenced is comparable. Furthermore, the line shape of the tails exhibits strong Voigt behavior. In this section, an exact modified Bessel functions expansion for the Voigt total and line-tail equivalent width is derived. Equations for the expansion coefficients are given for the pure Lorentz limit, for the pure Doppler limit and for Voigt line-tails with zero-to-moderate Doppler contributions.

The Problem

The objective of this section is to determine an accurate and efficient algorithm for evaluating the Voigt line shape absorption $W_\Delta = W_\Delta(Su, \gamma_c, \gamma_d)$ integrated between spectral frequencies v' and $\infty$ for a molecular transition centered at frequency $v_0$:

$$W_\Delta \equiv \int_\Delta^\infty [1 - \exp(-Suf_v)] dv \quad (3)$$

where the Voigt line-shape $f_v$ is the convolution of Lorentz and Doppler line-shape functions:

$$f_v = \frac{\gamma_c}{\pi^{3/2}} \int_{-\infty}^\infty \frac{\exp(-t^2)}{\gamma_c^2 + (v - \gamma_d t)^2} dt. \quad (4)$$

In these equations $\gamma_c \geq 0$ is the collision (Lorentz) half-width at "half" maximum [cm$^{-1}$], $\gamma_d \geq 0$ is the Doppler half-width at "1/e" of the maximum [cm$^{-1}$], $\Delta = v' - v_0$ is the spectral frequency displacement from line center [cm$^{-1}$], v is the spectral frequency integration variable [cm$^{-1}$], S is the line strength [atm$^{-1}$ cm$^{-2}$], and u is the column density [atm cm].

Since the Voigt line shape function $f_v$ is symmetric in v, the absorption term $W_{-\Delta}$ equals $2W_0 - W_\Delta$, and it suffices to restrict the analysis to $\Delta \geq 0$. For $\Delta \geq 0$, $W_\Delta$ is the (single-sided) line-tail absorption.

The Ladenburg and Reiche Function

Ladenburg and Reiche [see: R. Ladenburg and F. Reiche, Über selektive Absorption, *Ann. Phys.* 42, 181-209 (1913).] derived the exact expression for the total absorption ($N = -\infty$) from a Lorentzian line in terms of Bessel functions of the first kind with imaginary arguments:

$$W_{-\infty}^{Lorentz} = 2W_0^{Lorentz} = Su \exp\left(-\frac{Su}{2\pi\gamma_c}\right)\left[I_0\left(\frac{Su}{2\pi\gamma_c}\right) + I_1\left(\frac{Su}{2\pi\gamma_c}\right)\right] \quad (5)$$

(The modified Bessel functions, $I_0$ and $I_1$, can be evaluated using the polynomial approximations listed in Section 9.8 of Abramowitz and Stegun) [see: M. Abramowitz and I. A. Stegun, *Handbook of Mathematical Functions with Formulas, Graphs, and Mathematical Tables*, (New York, Dover Publications, 1965).] Ladenburg and Reiche also showed that the line-tail absorption $W_\Delta^{Lorentz}$ in the limit of $\Delta \gg \gamma_c$, i.e., where $f_v \cong \gamma_c/\pi v^2$, can be expressed in terms of an error function. In the next few sections, an expansion is derived for $W_\Delta^{Lorentz}$ that is exact for any spectral displacement $\Delta$.

Strategy for Determining $W_N$

In this section, the Ladenburg and Reiche formula is generalized to provide an exact modified Bessel function expansion for Voigt line-tail absorption. The line-tail absorption, Eq. (3), can be integrated by parts by setting $P = 1 - \exp(-Suf_v)$ and $dQ = dv$ and the integration variable switched from the frequency variable v to the Voigt line-shape function itself:

$$W_\Delta = Su \int_0^{f\Delta} v_f \exp(-Suf) df - \Delta[1 - \exp(-Suf_\Delta)] \quad (6)$$

Defining angle $\theta$ by the relationship $f(\theta) = f_{66}(1 - \cos\theta)/2$ and substituting into Eq. (6) gives $$W_\Delta = Suf_\Delta \exp\left(-\frac{Su}{2}f_\Delta\right)\int_0^\pi v_\theta \sin\left(\frac{\theta}{2}\right)\cos\left(\frac{\theta}{2}\right)\exp\left(\frac{Su}{2}f_\Delta\cos\theta\right)d\theta. \quad (7)$$

The coefficient of the exponential in the integrand is bounded for all $\theta$ between 0 and $\pi$. At $\theta = \pi$, $f$ equals $f_\Delta$, which implies that $v_{\theta = \pi}$ equals $\Delta$ and the coefficient equals zero. At $\theta = 0$, the situation is more complicated. Since the Voigt function $f$ is zero at $\theta = 0$, the spectral frequency v approaches infinity. However, this is exactly compensated by the sine term. With the boundedness of the coefficient established, a generalization of the Ladenburg and Reiche expression is obtained by expanding the coefficient of the exponential in the integrand of Eq. (7) (multiplied by $\pi f_\Delta$) in a Fourier series:

$$\pi f_\Delta v_\theta \sin\frac{\theta}{2}\cos\frac{\theta}{2} = \frac{V_0(\Delta)}{2} + \sum_{n=1}^{\infty} V_n(\Delta)\cos(n\theta) \qquad (8)$$

where $$V_n = V_n(\Delta) = f_\Delta \int_0^\pi v_\theta \sin\theta \cos(n\theta)\,d\theta \qquad (9)$$

Substituting Eq. (8) into Eq. (7) and noting the integral representation of the modified Bessel functions of integer order [Abramowitz and Stegun, Eq. 9.6.19], the desired expansion is obtained:

$$W_\Delta = Su\exp\left(-\frac{Su}{2}f_\Delta\right)\left[\frac{V_0}{2}I_0\left(\frac{Su}{2}f_\Delta\right) + \sum_{n=1}^{\infty} V_n I_n\left(\frac{Su}{2}f_\Delta\right)\right] - \Delta[1-\exp(-Suf_\Delta)] \qquad (10)$$

The higher order modified Bessel functions can be computed from $I_0(z)$ and $I_1(z)$ using the recurrence relationship [Abramowitz and Stegun, Eq. 9.6.26], although for small z, the ascending series [Abramowitz and Stegun, Eq. 9.6.10] is numerically more stable. With the Bessel functions defined, the calculation of Eq. (10) reduces to determining the Voigt line shape function at displacement frequency $\Delta$, i.e., $f_\Delta$ and to determining the Fourier coefficients $V_n$.

Computing the Fourier Coefficients

Determining the Fourier coefficients directly from Eq. (9) is complicated by the spectral frequency term. For the pure Doppler and Lorentz limits, the inversion is straightforward. However, in general, the calculation of the Fourier coefficients is greatly simplified by returning to spectral frequency as the dependent variable. This is accomplished by first substituting for angle $\theta$:

$$V_n = 2\int_0^{f\Delta v} v_f \cos(n\theta_f)\,df;\ \cos\theta_f = 1 - \frac{2f}{f_{\Delta v}} \qquad (11)$$

Next, integrate by parts with $Q=v_f=v$ and $dP_n=\cos(n\theta_f)df=\cos(n\theta_{f_v})df_v$:

$$V_n = 2vP_n\Big|_{v=\infty}^{v=\Delta v} + 2\int_{\Delta v}^{\infty} P_n\,dv. \qquad (12)$$

After expanding the $P_n$ integrals, the Fourier coefficients for $n\leq 7$ have the following form:

$$V_0 = 2F_0, \qquad (13a)$$

$$V_1 = V_0 - 2F_1, \qquad (13b)$$

$$V_2 = 4V_1 - 3V_0 + 16F_2/3, \qquad (13c)$$

$$V_3 = 6V_2 - 15V_1 + 10V_0 - 16F_3, \qquad (13d)$$

$$V_4 = 8V_3 - 28V_2 + 56V_1 - 35V_0 + 256F_4/5, \qquad (13e)$$

$$V_5 = 10V_4 - 45V_3 + 120V_2 - 210V_1 + 126V_0 - 512F_5/3, \qquad (13f)$$

$$V_6 = 12V_5 - 66V_4 + 220V_3 - 495V_2 + 792V_1 - 462V_0 + 4096F_6/7,\text{ and} \qquad (13g)$$

$$V_7 = 14V_6 - 91V_5 + 364V_4 - 1001V_3 + 2002V_2 - 3003V_1 + 1716V_0 - 2048F_7. \qquad (13h)$$

where $$F_n \equiv F_n(\Delta) \equiv \Delta f_\Delta + \frac{1}{f_\Delta^n}\int_\Delta^\infty f_v^{n+1}\,dv \qquad (14)$$

In this form, calculation of the Fourier coefficients reduces to determining Voigt function moment integrals, $F_n$.

Weak Line Limit

In the weak line limit, i.e. when Su is small, line absorption is known to be proportional to Su. Substituting $I_n(Suf_{66}/2) = [(Suf_\Delta/4)^n/n!]\{1+O[(Su)^2]\}$ into Eq. (10), the line tail absorption expression reduces to the correct weak line limit. The term $O(z^n)$ is used here and throughout to indicate terms of order $z^n$ and higher. In the total line absorption limit, $V_0(0)$ is one and $W_{-\infty}=2W_0$ equals Su to leading order.

Strong Line Limit

When the argument of the modified Bessel function is large, the value of the function is independent of n to leading order in $(1/z)$ [Abramowitz and Stegun, Eq. 9.7.1] with $e^{-z}I_n(z)\sim(2\pi z)^{-1/2}$. Thus, in the asymptotic limit the modified Bessel functions can be factored out of Eq. (10), leaving the sum of Fourier coefficients. Taking the $\theta$ approaches zero limit of Eq. (8), the Fourier coefficient sum becomes $$\frac{V_0(\Delta)}{2} + \sum_{n=1}^{\infty} V_n(\Delta) = \sqrt{\pi\gamma_c f_\Delta} \qquad (15)$$

Substituting this relationship into Eq. (10) results in the square root curve of growth:

$$W_\Delta + \Delta \sim \sqrt{Su\gamma_c}\left[1 + O\left(\frac{2}{Suf_\Delta}\right)\right];\ (\gamma_c > 0) \qquad (16)$$

For numerical implementations, it is recommended that the strong line limit be forced by setting a last Fourier coefficient by the constraint of Eq. (15).

The Lorentz Limit

In the Lorentz limit ($\gamma_d=0;\gamma_c>0$), the line-shape function has a simple form:

$$f_v^{Lorentz} = \frac{\gamma_c/\pi}{\gamma_c^2 + v^2} \quad (17)$$

It is convenient to define α as the ratio of the spectral displacement from line center Δ to the Lorentz half-width $\gamma_c$:

$$\alpha = \Delta/\gamma_c \quad (18)$$

The first six Fourier coefficients have the following form:

$$\frac{\pi V_0^{Lorentz}}{2} = \cot^{-1}\alpha + \frac{\alpha}{\alpha^2 + 1} \quad (19a)$$

$$\pi V_1^{Lorentz} = \alpha - (\alpha^2 - 1)\cot^{-1}\alpha \quad (19b)$$

$$\pi V_2^{Lorentz} = 2\alpha^3\left(\alpha\cot^{-1}\alpha - 1 + \frac{1/3}{\alpha^2 + 1}\right) \quad (19c)$$

$$\pi V_3^{Lorentz} = \alpha^3\left[5\alpha^2 + \frac{4}{3} - \alpha(5\alpha^2 + 3)\cot^{-1}\alpha\right] \quad (19d)$$

$$\pi V_4^{Lorentz} = 2\alpha^3\left[\alpha(7\alpha^4 + 8\alpha^2 + 2)\cot^{-1}\alpha - 7\alpha^4 - \frac{17}{3}\alpha^2 - \frac{11}{15} + \frac{1/15}{\alpha^2 + 1}\right] \quad (19e)$$

$$\pi V_5^{Lorentz} = \alpha^3\left[42\alpha^6 + 56\alpha^4 + \frac{301}{15}\alpha^2 + \frac{4}{3} - \alpha(42\alpha^6 + 70\alpha^4 + 35\alpha^2 + 5)\cot^{-1}\alpha\right] \quad (19f)$$

For $n \geq 2$, each of the $V_n^{Lorentz}$ are proportional to $\alpha^3$ and are small for $\Delta \ll \gamma_c$. However, for large α these expressions are numerically unstable. This limit is more easily evaluated using asymptotic series.

As suggested above, convergence to the strong line limit is forced by setting a final coefficient based on the normalization condition, Eq. (15). This is quite an important condition. The general approach for calculating the absorption integrals involves expanding the coefficient of the exponential in Eq. (7) in a Fourier series. However, in the strong line limit, the integrand is completely dominated by values near θ=0. The Fourier series fits the entire domain of θ values, giving no special weighting to the only part of the domain that significantly contributes for strong lines. The normalization constraint helps tailor the fit in this region.

Figure 5:
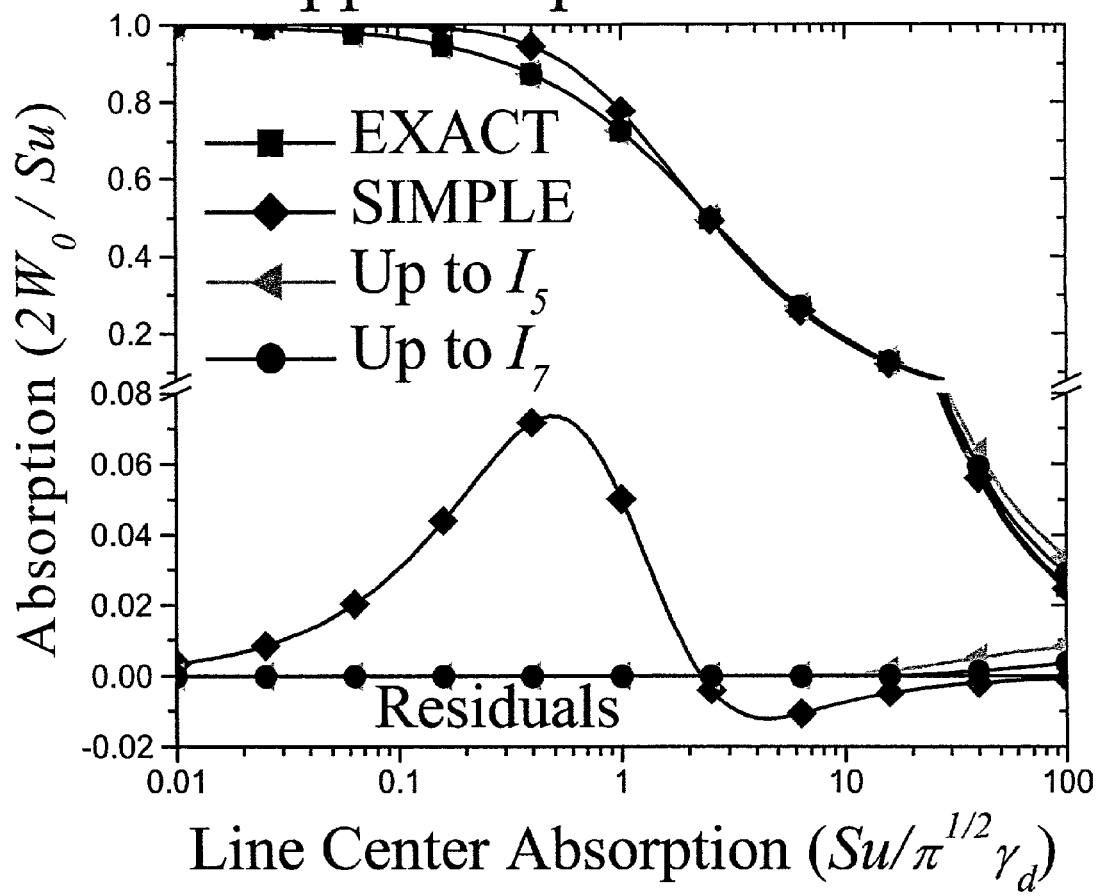
FIG. 5 shows the in-band transmittance as a function of bandwidth for a pure Lorentz line with half-width 0.1 $cm^{-1}$. Results are illustrated for line center optical depths of 0.04 (squares), 0.2 (circles), 1 (up_arrow), 5 (down_arrow), 25 (diamond) and 125 (left_arrow). The thick curves with symbols are the results from the modified Bessel function expansion truncated at $I_6$, and the thin curves without symbols are the results computed assuming line tails are inversely proportional to frequency squared.

In FIG. 5, the in-band transmittance is plotted as a function of band half-width. The In-band transmittance increases as bandwidth increases. If the bandwidth is a factor of 3 to 4 times larger than the Lorentz half-width, the line tails can be reasonably well represented by the reciprocal-frequency squared relationship (dashed curves). For narrower band models, this relationship breaks down and the exact expansion is required.

Figure 6:
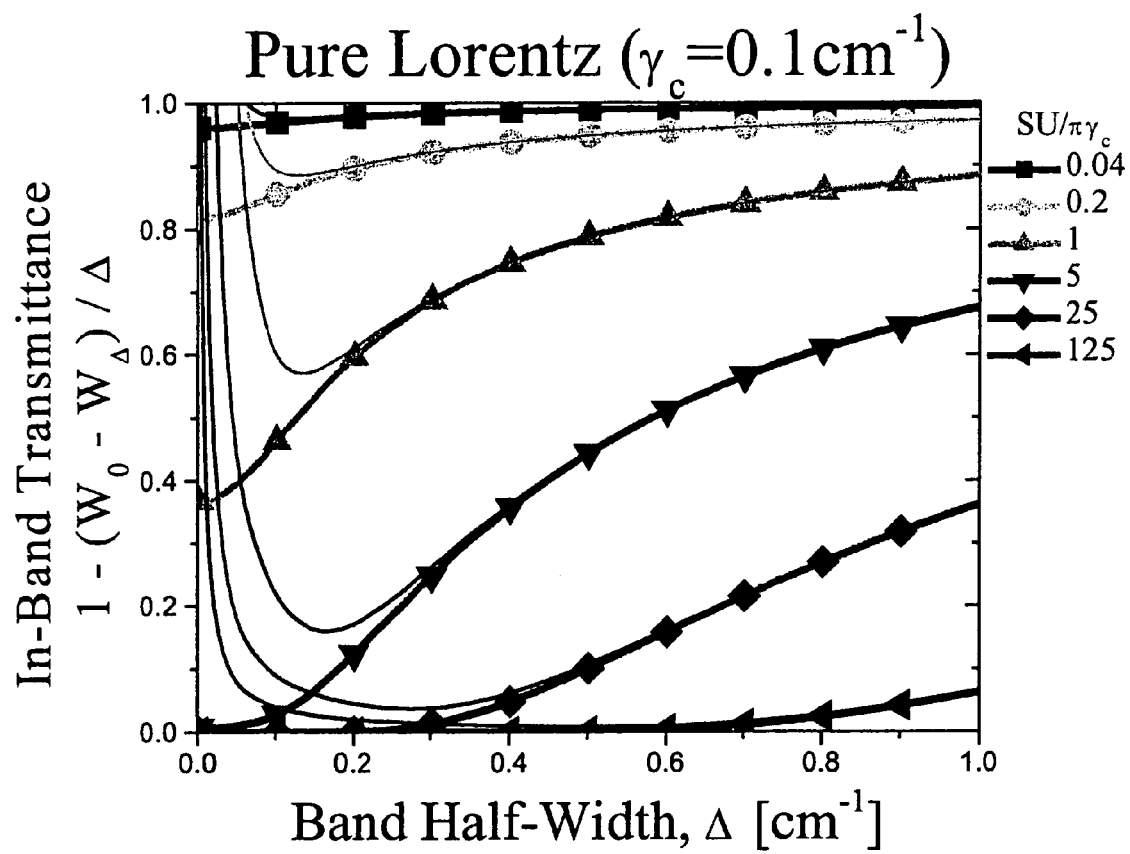
FIG. 6 shows the in-band transmittance as a function of line center absorption for a pure Lorentz line with half-width 0.1 $cm^{-1}$. Results are illustrated for bandwidths of 6.4 (squares), 1.6 (circles), 0.4 (up_arrow), 0.1 (down_arrow) and 0.025 (diamond) $cm^{-1}$, and for modified Bessel function expansions up to $I_2$ (thin_dash), $I_4$ (solid_line) and $I_6$ (line_with_symbols).

The convergence of the Lorentz equivalent width expansion is illustrated by FIG. 6. In each of the curves, the final Lorentz Fourier coefficient is computed using the normalization sum Eq. (15) rather than the exact value from Eq. (19) to insure proper convergence in the strong line limit. In-band transmittances above 5% are accurately computed using just 3 terms in the modified Bessel function expansion, up to $I_2$. Adding two more terms, the expansion is accurate for transmittances above about ½%. Using all 7 terms defined above, the predictions are accurate for all transmittances above 0.001.

In generating the 7-term curves, the predicted transmittances were compared to the maximum $\exp(-Suf_{66}^{Lorentz})$ and minimum $\exp(-Suf_0^{Lorentz})$ possible transmittance values, and replaced by the average of the extreme values when the prediction lied outside this range. This replacement was only necessary for transmittances below 0.001 (not for values shown in FIG. 6). Even though convergence to the strong line limit is guaranteed by the normalization condition, there is an intermediate region for very small transmittances where predictions diverge slightly. Transmittance errors as large as 0.004 can result for transmittances near or below 0.00001.

Pure Doppler Limit

In this section, the expression for the Voigt line-tail absorption, Eq. (10), is applied to a pure Doppler line ($\gamma_c$=0). In this limit, the line shape function has the following form:

$$f_v^{Doppler} = \frac{\exp(-b_v)}{\gamma_d\sqrt{\pi}}; b_v \equiv \frac{v^2}{\gamma_d^2}. \quad (20)$$

Inserting this definition into Eq. (14), the Voigt function moment integrals have a relatively simple form:

$$F_n^{Doppler} = \sqrt{\frac{b_\Delta}{\pi}} \exp(-b_\Delta)\left[1 + \frac{1}{2}\sqrt{\frac{\pi}{nb_\Delta}} \exp(nb_\Delta)erfc\sqrt{nb_\Delta}\right] \quad (21)$$

The Doppler Fourier coefficients are computed by directly substituting these moment integrals into Eq. (13).

In the limit of total Doppler line absorption, the complementary error function terms are all one (since $b_0$=0), and the following expression results for the total Doppler equivalent width:

$$W_{-\infty}^{Doppler} = 2W_0^{Doppler} = Su\exp\left(\frac{-Su}{2\gamma_d\sqrt{\pi}}\right)\begin{bmatrix}I_0\left(\frac{Su}{2\gamma_d\sqrt{\pi}}\right)+ \\ 0.58578644I_1\left(\frac{Su}{2\gamma_d\sqrt{\pi}}\right) - 0.57765281I_2\left(\frac{Su}{2\gamma_d\sqrt{\pi}}\right) - \\ 0.25271345I_3\left(\frac{Su}{2\gamma_d\sqrt{\pi}}\right) - 0.14605219I_4\left(\frac{Su}{2\gamma_d\sqrt{\pi}}\right) - \\ 0.09628129I_5\left(\frac{Su}{2\gamma_d\sqrt{\pi}}\right) - 0.06867590I_6\left(\frac{Su}{2\gamma_d\sqrt{\pi}}\right) - \\ 0.05165314I_7\left(\frac{Su}{2\gamma_d\sqrt{\pi}}\right) + \ldots\end{bmatrix} \quad (22)$$

All the coefficients in this expansion can be represented analytically.

Applying the strong line limit, Eq. (15), to pure Doppler lines indicates that the $V_n^{Doppler}$ coefficients must sum to zero to avoid a square root curve of growth. The coefficients actually included in Eq. (22) sum to −0.107. Since the sum must approach zero, terms beyond those listed in Eq. (22) cannot all negative.

Figure 7:
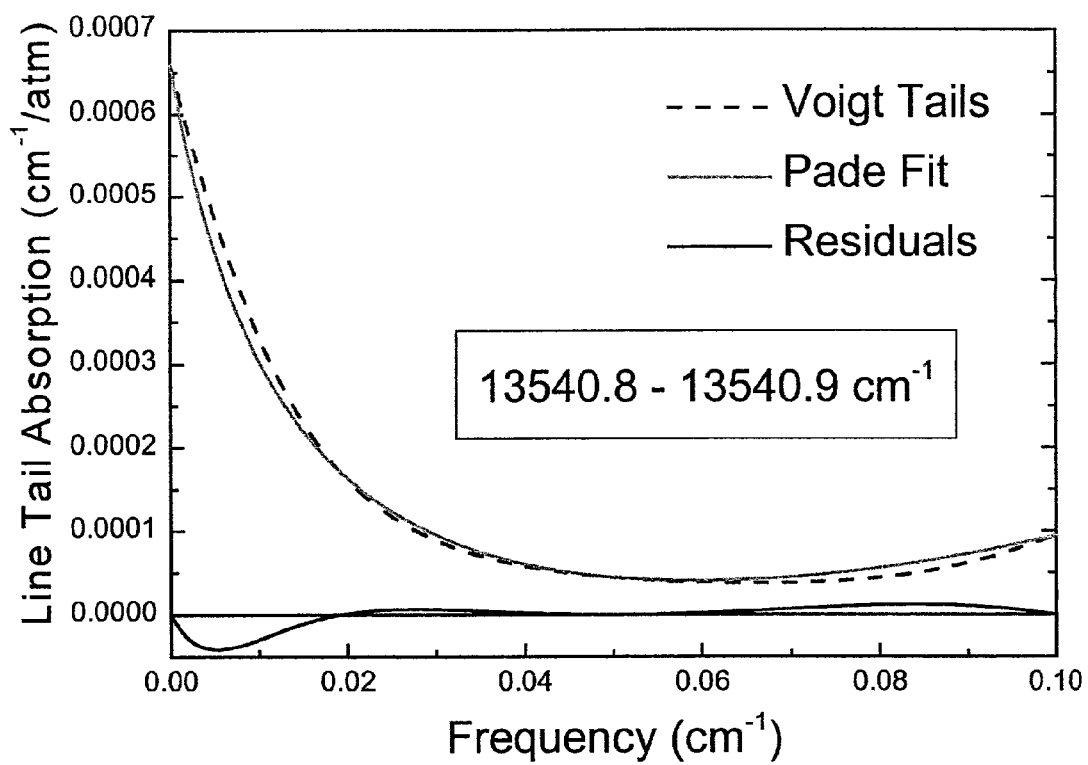
FIG. 7 shows Doppler total equivalent width predictions as a function of line center absorption. The modified Bessel function expansions truncated at $I_5$ and $I_7$, and a simple weak-line to strong-line interpolation formula is compared the exact result. Note the curves have been plotted with a break in the ordinate scale at 0.08 in order to accentuate the residuals.

The accuracy of the truncated series Eq. (22) for calculation of the Doppler total equivalent width is illustrated in FIG. 7. For comparison, results are also presented for an often-used simple interpolation formula between the weak and strong line Doppler limits:

$$W_{-\infty}^{Doppler} \approx \gamma_d\sqrt{2\ln\left(1 + \frac{1}{2}(Su/\gamma_d)^2\right)} \quad (23)$$

If line center absorption $Su/\gamma_d\sqrt{\pi}$ is less than 10, the result from using the first 6 terms in Eq. (22), i.e., up to $I_5$, is essentially exact. For even stronger lines, errors quickly become appreciable. For a line center extinction of 100, the 6 and 8 term expansions produce 24.2% and 12.5% errors, respectively. In this limit, the asymptotic expansion [see: C. B. Ludwig, W. Malkmus, J. E. Reardon, and J. A. L. Thomson, "Handbook of Infrared Radiation from Combustion Gases, Ed. R. Goulard and J. A. L. Thomson, NASA SP-3080 (1973), Eq. 2-B-2] or even Eq. (23) is preferable.

Voigt Line Tails with Moderate Doppler Dependence

The objective of this section is to obtain an analytic expression for the Fourier coefficients $V_n$ of Eq. (10) for Voigt lines with at most moderate Doppler dependence. To be more specific, the analysis is restricted to line tails $W_\Delta$ for which $x_\Delta$ is large, where $$a \equiv \frac{\gamma_c^2}{\gamma_d^2}; x_v \equiv a + b_v = \frac{\gamma_c^2 + v^2}{\gamma_d^2}. \quad (24)$$

From Eq. (13), the calculation of the Fourier coefficients reduces to calculation of the Voigt function moment integrals of Eq. (14), $F_n$. To derive an expression for these integrals, a workable form for the Voigt line shape must be derived. It follows from Eq. (4) that the Voigt line shape is proportional to the real part of the complex probability function $w(z_v)$ [Abramowitz and Stegun, Eq. 7.4.13]. From the continued fraction representation for $w(z_v)$ [Abramowitz and Stegun, Eqs. 7.1.4 and 7.1.15], the Voigt integral can be expanded in an asymptotic series:

$$f_v \sim \frac{a/x_v}{\pi\gamma_c}\begin{bmatrix}1 + \frac{1}{x_v}\left(\frac{3}{2} - 2\frac{a}{x_v}\right) + \frac{1}{x_v^2}\left(\frac{15}{4} - 15\frac{a}{x_v} + 12\frac{a^2}{x_v^2}\right) + \\ \frac{1}{x_v^3}\left(\frac{105}{8} - 105\frac{a}{x_v} + 210\frac{a^2}{x_v^2} - 120\frac{a^3}{x_v^3}\right) + O(x_v^{-4})\end{bmatrix} \quad (25)$$

The expression for $f_v$ can now be raised to the $n^{th}$ power, expanded in powers of $1/x_v$, and integrated to give the result:

$$\pi(\pi\gamma_c)^n\int_\Delta^\infty f_v^{n+1}dv = \quad (26)$$

$$\int_{\arctan(\alpha)}^{\pi/2}\left\{\begin{array}{c}\cos^{2n}\phi - \frac{n(n+1)}{2(n+2)}\left(\frac{1+a^2}{x_\Delta}\right)\cos^{2n+2}\phi + \\ \frac{n(n+1)(n+2)(n+3)}{8(n+3)(n+4)}\left(\frac{1+a^2}{x_\Delta}\right)^2\cos^{2n+4}\phi - \\ \frac{n(n+1)(n^4+26n^3+251n^2+874n+1008)}{48(n+4)(n+5)(n+6)}\left(\frac{1+a^2}{x_\Delta}\right)^3\cos^{2n+6}\phi\end{array}\right\}d\phi +$$

-continued $$\frac{(n+1)\alpha/x_\Delta}{(n+2)(1+\alpha^2)^{n+1}} - \left(\frac{n+6}{1+\alpha^2} - \frac{n^2+8n+19}{2(n+3)}\right)\frac{(n+1)\alpha/x_\Delta^2}{(n+4)(1+\alpha^2)^{n+1}} +$$

$$\left(\begin{array}{c}\dfrac{2(n^2+17n+90)}{3(1+\alpha^2)^2} - \dfrac{5n^3+99n^2+706n+1800}{6(n+5)(1+\alpha^2)} + \\ \dfrac{7n^4+144n^3+1127n^2+3942n+5400}{24(n+4)(n+5)(1+\alpha^2)}\end{array}\right)\dfrac{(n+1)\alpha/x_\Delta^3}{(n+6)(1+\alpha^2)^{n+1}} + O(x_\Delta^{-4})$$

where $\alpha$ is the ratio defined in Eq. (18) and the cosine integrals can be analytically evaluated:

$$\int_{\arctan(\alpha)}^{\pi/2} \cos^{2m}\phi\, d\phi = \frac{(2m)!}{4^m(m!)^2}\left\{\cot^{-1}\alpha - \frac{\alpha}{1+\alpha^2}\sum_{r=0}^{m-1}\frac{(r!)^2}{(2r+1)!}\left(\frac{4}{1+\alpha^2}\right)^r\right\} \quad (27)$$

These expressions can now be substituted into Eqs. (13) and (14) to compute the Fourier coefficients.

If the Lorentz half-width is large compared to the Doppler half-width, then $x_\Delta$ is large even when $\Delta$ is zero and the equations of this section can be used to evaluate the total Voigt equivalent width. In this limit, the expression for the Voigt function moment integrals simplify considerably and the Voigt equivalent width series to order $O(x^{-4})$ actually truncates after a finite number of terms.

Summarizing the Algorithm

A generalization of the Ladenburg and Reiche absorption formula to Voigt lines and their line-tails has been derived. Given the column strength Su, the Lorentz half-width $\gamma_c$, the Doppler half-width $\gamma_d$ and the line-tail spectral displacement $\Delta$, an exact expansion for the line-tail absorption $W_\Delta$ is given by Eq. (10). The Voigt line-shape function $f_\Delta$ at spectral frequency $\Delta$ can either be computed using the asymptotic series of Eq. (25), or more accurately using the Humlíček rational approximation [see: J. Humlíček, "An Efficient Method for Evaluation of the Complex Probability Function: The Voigt Function and it Derivatives", J. Quant. Spectrosc. Radiat. Transfer 21, 309-313 (1979)]. For the special case of spectral frequency $\Delta=0$, the Voigt line-shape is conveniently computed from its complementary error function representation. The modified Bessel function terms $e^{-z}I_n(z)$ for real z can be computed using polynomial approximations [Abramowitz and Stegun, Sec. 9.8], recurrence relations, and/or ascending series. To define the Voigt Fourier coefficients $V_n$, the variables $\alpha$, $\alpha$ and $x_v$ [Eqs. (18) and (24)] are introduced. The Voigt Fourier coefficients are defined as an asymptotic series in $1/x_v$ [Eqs. (13)-(14)], which themselves depend on the Voigt moment integrals, Eqs. (26)-(27). For the limiting cases of pure Lorentz and pure Doppler lines, exact expressions are derived for the Fourier coefficients, Eqs. (19) for the Lorentz case, and Eq. (21) for the Doppler case.

Many radiative transfer problems require calculation of the single-line finite-spectral-bin equivalent width $W_{sl}$. For a finite spectral interval containing a line-centered $\Delta$ wavenumbers from the left edge and $\Delta'$ wavenumbers from the right edge, the single-line equivalent width equals the sum of the contributions from the two sides of the line, $(W_0-W_\Delta)+(W_0+W_{\Delta'})$. If the Lorentz half-width is significantly larger than the Doppler half-width, $x_0$ is large and all of the absorption terms can be computed using the formalism described here. On the other hand, if $x_\Delta$ (or $x_{\Delta'}$) is large but $x_0$ is not, the total Voigt equivalent width $2W_0$ can be estimated using the Rodgers and Williams interpolation formula [C. D. Rodgers and A. P. Williams, (1974)], with the Lorentz total equivalent width computed from the Ladenburg and Reiche formula and the Doppler equivalent width obtained from either Eq. (22) above or from strong line limit expression (e.g., Su>22.346 $\gamma_d \sqrt{\pi}$) [Eq. (2-B-2) in C. B. Ludwig, et al., 1973]. Finally, if $x_\Delta$ (or $x_{\Delta'}$) is not large, then the spectral bin half width $\Delta$ is comparable to or smaller than the Doppler half-width $\gamma_d$. In this limit, the Voigt line-shape is relatively flat within the interval and a numerical integration using the Humlíček rational approximation for the line shape should converge rapidly with only a few evaluations.

SERTRAN Validation

SERTRAN validation efforts have concentrated on the LWIR through SWIR spectral regions, and all validations shown here were performed with the "double-bin" band model approach. SERTRAN was validated by comparison to predictions of the FASE LBL model and to measurements from the High-resolution Interferometer Sounder (HIS) Fourier Transform Spectrometer [see H. E. Revercomb, H. Bujis, H. B. Howell, R. O. Knuteson, D. D. LaPorte, W. L. Smith, L. A. Sromovsky, and H. W. Woolf,: "Radiometric calibration of IR interferometers: Experience from the High-Resolution Interferometer Sounder (HIS) aircraft instrument," RSRM '87, Advances in Remote Sensing Retrieval Methods. A. Deepak, H. Fleming, and J. Theon, Eds. 1989]. The FASE model has itself been extensively validated against measured data, and it provides the benchmark for determining the accuracy of the SERTRAN band model results. The HIS spectrometer measures high quality, sub-wavenumber calibrated spectral radiances between 600 and 2700 cm$^{-1}$ (3.7 to 16.7 µm) for direct validation.

SERTRAN to FASE Validations

SERTRAN and FASE spectral transmittance predictions were compared for frequencies between 500 and 4000 cm$^{-1}$ (2.5 to 20 µm) and for horizontal (constant pressure) paths between 0 and 40 km altitude. Path lengths were selected to produce band average transmittances near 50% because transmittance residuals tend to be largest for transmittances near 0.5.

Figure 8:
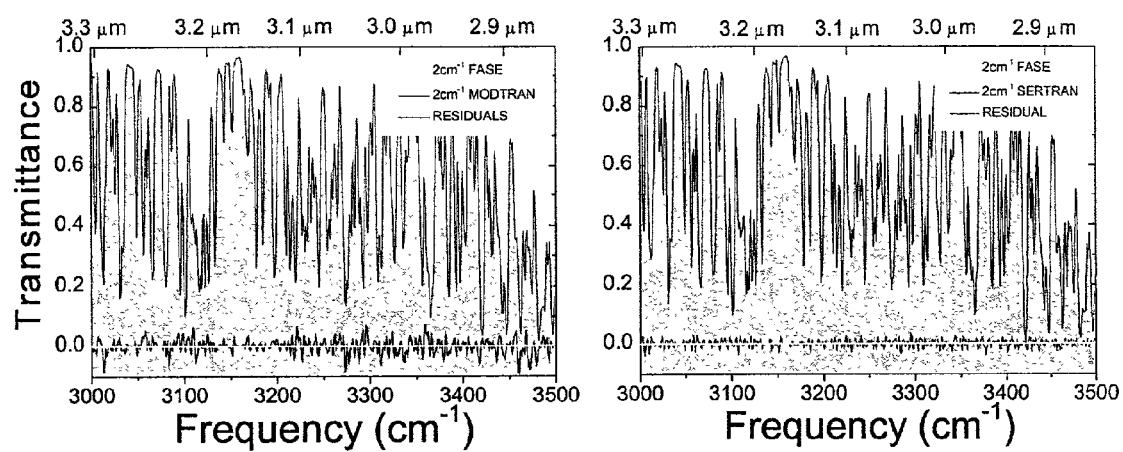
FIG. 8 shows Validation Results for MODTRAN (left) and SERTRAN (right). The band model spectral transmittances are compared to FASE LBL predictions for a 0.5-km path at the ground. The results from all three models were convolved with the same 2 $cm^{-1}$ spectral response function.

SERTRAN models line correlation and overlap more accurately than MODTRAN because of its higher spectral resolution. Also, the SERTRAN line tail algorithm improves upon the MODTRAN algorithm. Thus, the SERTRAN to FASE residuals will be smaller than MODTRAN to FASE residuals when all three calculations are degraded to a common spectral resolution. This is illustrated in FIG. 8. Spectral transmittances are compared for the 0.5 km horizontal path at 1 atm pressure containing U.S. Standard profile $H_2O$, $CO_2$, and $O_3$ concentrations. High spectral resolution SERTRAN and FASE predictions were convolved with a non-overlapping 1 $cm^{-1}$ rectangular slit, and subsequently degraded using a 2 $cm^{-1}$ triangular slit to mimic the MODTRAN 2 $cm^{-1}$ result. For both MODTRAN and SERTRAN, no strong bias is observed, i.e., the residual curves straddle the zero residual line. However, sporadic MODTRAN residuals approach 0.1 while all the 2 $cm^{-1}$ SERTRAN residuals are under 0.02.

Figure 9:
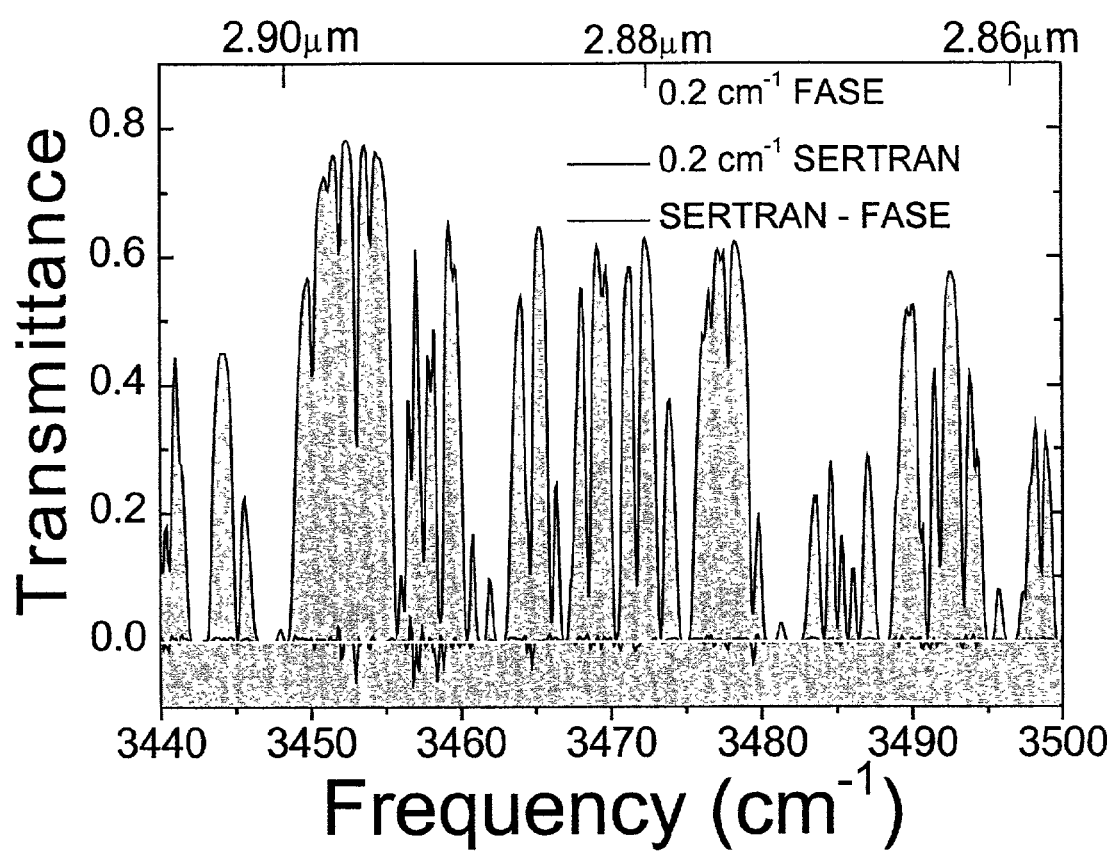
FIG. 9 is a comparison of FASE and SERTRAN 0.2 $cm^{-1}$ Spectral Transmittances near 2.88 µm.

SERTRAN is compared to FASE at 0.2 $cm^{-1}$ spectral resolution in FIG. 9. The scenario is identical to that of FIG. 8, a ½-km ground path with $H_2O$, $CO_2$, and $O_3$. The spectral range has been reduced so that spectral details can be resolved. For much of the spectrum the residuals are under 0.01, but occasional spikes are large as 0.07 are evident, consistent with the accuracy of the equivalent width residuals calculations.

Figure 10:
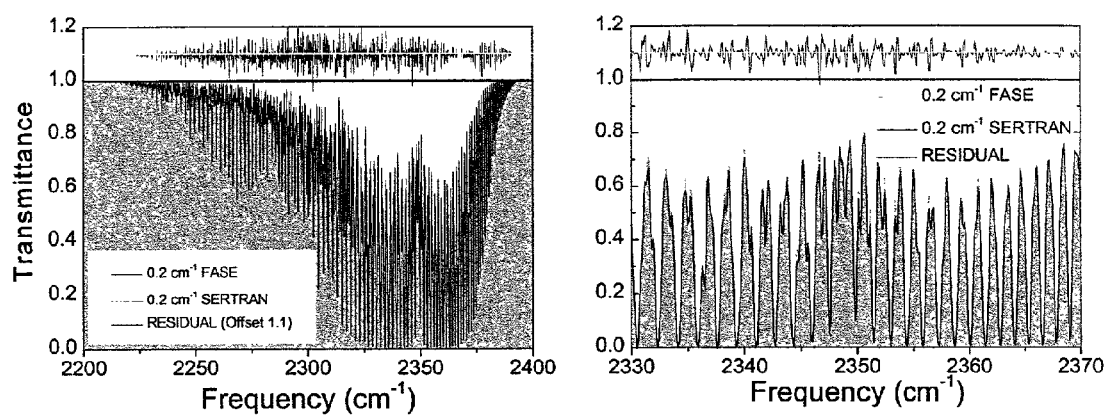
FIG. 10 shows FASE and SERTRAN 0.2 $cm^{-1}$ Spectral Transmittances for $CO_2$ at 40-km Altitude and a 100-km Constant Pressure Path. The results are illustrated for the entire 4.3-µm band (left) and an enlargement for the center of the band (right).

Basic to the SERTRAN band model is the premise that molecular line absorption is substantial within two 0.1 $cm^{-1}$ spectral bins. At higher altitudes, this assumption breaks down—molecular line widths are small compared to the 0.1 $cm^{-1}$ bandwidth and most of the individual line absorption occurs in a single bin. As a result, SERTRAN essentially becomes a 0.2 $cm^{-1}$ band model. This is illustrated in FIG. 10. SERTRAN 0.2 $cm^{-1}$ spectral transmittances are compared to FASE results for a horizontal path at 40-km altitude and with a 100-km range. The residuals are larger than at lower altitudes. Individual narrow yet strong absorption lines are equally partitioned into two 0.1 $cm^{-1}$ spectral bins yielding too much absorption in one bin and too little in its neighbor.

SERTRAN to HIS Validations

SERTRAN predictions were compared to HIS spectrometer measurements [see H. E. Revercomb, H. Bujis, H. B. Howell, R. O. Knuteson, D. D. LaPorte, W. L. Smith, L. A. Sromovsky, and H. W. Woolf,: "Radiometric calibration of IR interferometers: Experience from the High-Resolution Interferometer Sounder (HIS) aircraft instrument," RSRM '87, *Advances in Remote Sensing Retrieval Methods*. A. Deepak, H. Fleming, and J. Theon, Eds. 1989] from two separate campaigns: an airborne nadir measurement from 20-km altitude over the Pacific Ocean (Apr. 14, 1986) and a ground-based zenith measurement from the GAPEX experiment in Denver (Oct. 31, 1988). For both campaigns, atmospheric temperature and $H_2O$ profiles were derived from radiosonde data. The validation results from the two sets of comparisons are similar. The results are presented from the nadir measurement comparison, for which a FASE validation was previously performed. [See: J. Wang, G. P. Anderson, H. E. Revercomb, and R. O. Knuteson, "Validation of FASCOD3 and MODTRAN3: Comparison of Model Calculations with Ground-Based and Airborne Interferometer Observations Under Clear-Sky Conditions," *Appl. Optics*, 35, pp. 6028-6040, 1996].

Figure 11:
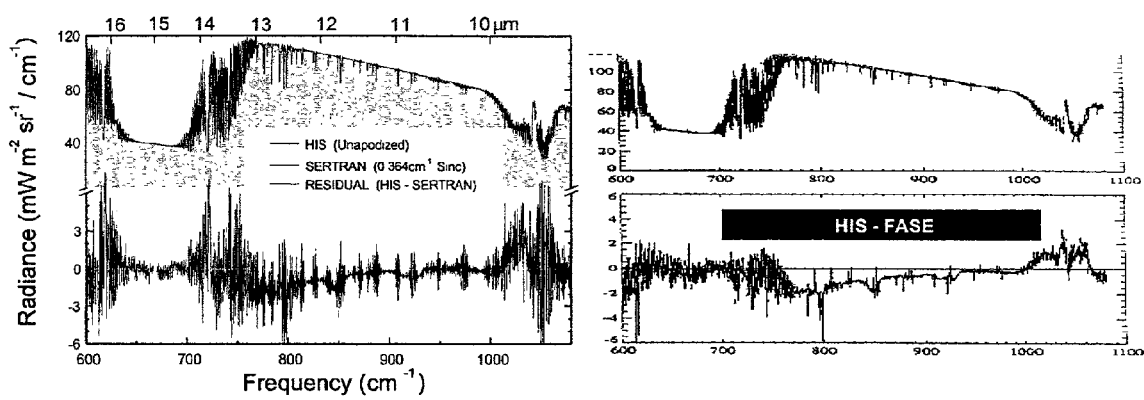
FIG. 11 shows LWIR Validation of SERTRAN (left) and FASE (right) Spectral Radiances Against HIS Spectrometer Measurements for Nadir Viewing from 20-km Altitude over the Pacific Ocean (Apr. 14, 1986). SERTRAN radiances were convolved assuming a 0.364 $cm^{-1}$ (FWHM) Sinc function.

HIS measurements for the 600-1080 $cm^{-1}$ spectral band and the SERTRAN and FASE predictions are illustrated in FIG. 11. The upper curves overlay the measured and modeled spectral radiances; the lower curves contain the measurement minus model residuals plotted with matched vertical scales. The HIS minus SERTRAN residuals are at the few percent level with spectral radiances and residuals near 80 and 3 mW $m^{-2}$ $sr^{-1}/cm^{-1}$, respectively. The unapodized HIS Fourier transform spectra were reported to have 0.364 $cm^{-1}$ spectral resolution in this band.

For these comparisons, the SERTRAN results were computed using a 0.364 $cm^{-1}$ full width at half maximum (FWHM) sinc function. The results seem to indicate a mismatch in the filter function—the residuals contain more jitter than the earlier SERTRAN to FASE comparisons would suggest. Nevertheless, the agreement is good. Both SERTRAN and FASE modeled the sea surface as a blackbody (unit emissivity) which accounts for the baseline offset between 800 and 1000 $cm^{-1}$. The residual spectrum between 1000 and 1080 $cm^{-1}$ indicates that the $O_3$ column amount was overestimated in the models—the main effect of the ozone is to attenuate the surface signal, and lowering the column amount should eliminate the 9.6 μm $O_3$ band spectral feature.

Figure 12:
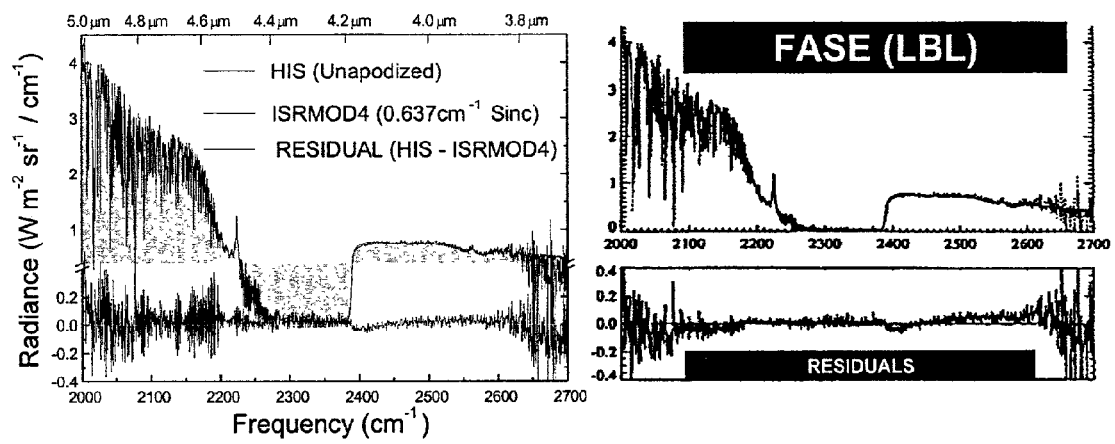
FIG. 12 shows SWIR Validation of SERTRAN (left) and FASE (right) Spectral Radiances Against HIS Spectrometer Measurements for Nadir Viewing from 20-km Altitude over the Pacific Ocean (Apr. 14, 1986).

In the short-wave IR, the HIS spectrometer has a band extending from 2000 to 2700 $cm^{-1}$, 3.7 to 5.0 μm, with a reported spectral resolution of 0.637 $cm^{-1}$. Below around 4.0 μm, the solar components become important for daytime measurements. FASE includes the solar reflection off the surface in its nadir atmospheric radiance calculations (ocean surface albedo set to 5% in the SWIR model calculations), but atmosphere scattered solar radiance contributions are neglected. SERTRAN, like MODTRAN, includes the atmospheric scattered contributions in its calculations. This is evident in the SWIR HIS comparison, FIG. 12. Between 2400 and 2600 $cm^{-1}$ FASE slightly under-predicts the spectral radiance. Although the SERTRAN predictions are noisier, the small bias in this region is decreased. This result had previously been demonstrated using MODTRAN, albeit with the spectral data degraded to 2 $cm^{-2}$. The SERTRAN comparison has more jitter than the FASE comparison, especially between 2000 and 2200 $cm^{-1}$, but again this is most likely due to a spectral filter mismatch. Otherwise, the SERTRAN and FASE results are comparable.

The reformulation of the MODTRAN band model and development of SERTRAN together provide a basis for future, rapid sub-wavenumber radiative transport analysis in the terrestrial atmosphere. The low-altitude IR validations performed to date demonstrate that SERTRAN achieves MODTRAN accuracy but at higher spectral resolution, with band average transmittance residuals of order 0.01 or better. Furthermore, comparisons of SERTRAN to MODTRAN at a common spectral resolution ($\geqq 2$ $cm^{-1}$) show approximately a 4-fold decrease in residuals.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. A band model method for determining individual atomic and molecular species spectral transmittances through a gaseous medium, the method comprising the steps of:

providing atomic and molecular transition data for a given spectral range and atmospheric conditions;

selecting a spectral region to be considered;

dividing the spectral region into a number of spectral bins that determine a spectral resolution, each bin having a width of about 0.1 $cm^{-1}$ or less;

calculating atomic and molecular species line center absorption from at least an equivalent width of the atomic and molecular transitions centered within each spectral bin;

calculating line tail absorption within each spectral bin from atomic and molecular transitions not centered within the bin;

determining atomic and molecular species spectral transmittances for each spectral bin, the spectral transmittance having a value which is a function of at least the calculated line center absorptions and the calculated line tail absorptions; and outputting the determined spectral transmittances.

2. The method of claim 1 wherein the calculating line center absorption step includes calculating, from an exact expansion, a bin Voigt equivalent width of atomic and molecular transitions whose centers lie within the spectral bin.

3. The method of claim 2, wherein the exact expansion is an exact modified Bessel functions expansion.

4. The method of claim 2, wherein the calculating line tail absorption step includes subtracting line-tail absorption as calculated from a column strength, a Lorentz half-width, a Doppler half-width, and a line tail spectral displacement.

5. The method of claim 2, wherein the calculating line center absorption step includes determining a Voigt line-shape function computed at specific frequencies.

6. The method of claim 1, wherein the line tail calculation step includes calculating line tail absorption within each bin from atomic and molecular transitions centered outside of the bin using Padé approximant spectral fits to Voigt absorption coefficient curves.

7. The method of claim 6, wherein the line tail absorption calculation step includes determining a database of temperature and pressure dependent Padé approximant spectral fits to Voigt absorption coefficient curves.

8. The method of claim 7, wherein there are five Padé parameters.

9. The method of claim 7, wherein Padé parameters are determined from summed line tail spectral absorption coefficients.

10. The method of claim 9, wherein each bin has a center and two edges, and one Padé parameter is determined at the center of the bin, and one at each edge of the bin.

11. The method of claim 9, wherein one Padé parameter is the derivative of the absorption coefficient with respect to a normalized spectral variable at the line center.

12. The method of claim 9, wherein one Padé parameter is the integral of the spectral absorption coefficient over a spectral band.

13. The method of claim 7, wherein the Padé database is generated for a plurality of temperatures.

14. The method of claim 7, wherein the Padé database is determined for a plurality of pressures.

15. The method of claim 1, wherein the line center absorptions are calculated from atomic and molecular transitions centered no more than half a spectral bin width from the bin, and the line tail absorptions are calculated from atomic and molecular transitions not centered within a half spectral bin width from the bin.

16. A method for computing the contribution of line centers to a determination of individual atomic and molecular species spectral transmittances through a gaseous medium, the method comprising the steps of:

providing atomic and molecular transition data for a given spectral range and atmospheric conditions;

selecting a spectral region to be considered;

dividing the spectral region into a number of spectral bins that determine a spectral resolution, each bin having a width of about $0.1 \text{ cm}^{-1}$ or less;

calculating a bin Voigt equivalent width of atomic and molecular transitions centered within each spectral bin from an exact expansion;

determining atomic and molecular species spectral transmittances for each spectral bin, the spectral transmittance having a value which is a function of at least the calculated equivalent widths; and outputting the determined spectral transmittances.

17. The method of claim 16, wherein the exact expansion is an exact modified Bessel functions expansion.

18. The method of claim 16, wherein the calculating step includes subtracting line-tail absorption as calculated from a column strength, a Lorentz half-width, a Doppler half-width, and a line tail spectral displacement.

19. The method of claim 16, wherein the calculating step includes determining a Voigt line-shape function computed at specific spectral frequencies.

20. A method for computing the contribution of line tails to the determination of individual atomic and molecular species spectral transmittances through a gaseous medium, the method comprising the steps of:

providing atomic and molecular transition data for a given spectral range and atmospheric conditions;

selecting a spectral region to be considered;

dividing the spectral region into a number of spectral bins that determine a spectral resolution, each bin having a width of about $0.1 \text{ cm}^{-1}$ or less;

calculating line tail absorption within each bin from atomic and molecular transitions centered outside of the bin using Padé approximant spectral fits to Voigt absorption coefficient curves;

determining atomic and molecular species spectral transmittances for each spectral bin, the spectral transmittance having a value which is a function of at least the calculated line tail absorptions; and outputting the determined spectral transmittances.

21. The method of claim 20, wherein the calculating step includes determining a database of temperature and pressure dependent Padé approximant spectral fits to Voigt absorption coefficient curves.

22. The method of claim 21, wherein there are five Padé parameters.

23. The method of claim 21, wherein Padé parameters are determined from summed line tail spectral absorption coefficients.

24. The method of claim 23, wherein each bin has a center and two edges, and one Padé parameter is determined at the center of the bin, and one at each edge of the bin.

25. The method of claim 21, wherein one Padé parameter is the derivative of the absorption coefficient with respect to a normalized spectral variable at the line center.

26. The method of claim 21, wherein one Padé parameter is the integral of the spectral absorption coefficient over a spectral band.

27. The method of claim 21, wherein the Padé database is generated for a plurality of temperatures.

28. The method of claim 21, wherein the Padé database is determined for a plurality of pressures.

* * * * *